United States Patent [19]
Hershberger et al.

[11] Patent Number: 5,977,746
[45] Date of Patent: Nov. 2, 1999

[54] RECHARGEABLE BATTERY PACK AND METHOD FOR MANUFACTURING SAME

[75] Inventors: David E. Hershberger, Paw Paw; John Izenbaard, Vicksburg, both of Mich.

[73] Assignee: Stryker Corporation, Kalamazoo, Mich.

[21] Appl. No.: 09/120,093

[22] Filed: Jul. 21, 1998

[51] Int. Cl.$^6$ .......................... H01M 10/44; H01M 10/46
[52] U.S. Cl. .............................. 320/112; 320/116; 429/99; 429/100; 429/149
[58] Field of Search ..................... 320/107, 110, 320/112, 113, 116; D13/103, 104, 105; 429/7, 96, 99, 100, 149, 151, 152, 153, 156

[56] References Cited

U.S. PATENT DOCUMENTS

| | | | |
|---|---|---|---|
| 1,509,209 | 9/1924 | Huntley | 429/117 |
| 2,058,755 | 10/1936 | Arnesen | 320/112 X |
| 3,518,524 | 6/1970 | Roszyk | 320/112 X |
| 4,147,838 | 4/1979 | Leffingwell . | |
| 4,383,011 | 5/1983 | McClelland et al. | 429/94 X |
| 4,407,911 | 10/1983 | Hooke | 429/99 X |
| 4,608,528 | 8/1986 | Stillwell | 320/113 |
| 5,089,738 | 2/1992 | Bergqvist et al. . | |
| 5,191,275 | 3/1993 | Singhal | 320/112 |
| 5,192,904 | 3/1993 | Leiserson | 320/112 |
| 5,207,697 | 5/1993 | Carusillo et al. . | |
| 5,545,491 | 8/1996 | Farley | 429/7 |

FOREIGN PATENT DOCUMENTS

| | | |
|---|---|---|
| 0 255 631 | 2/1988 | European Pat. Off. . |
| 33 17 398 | 11/1984 | Germany . |

Primary Examiner—Edward H. Tso
Attorney, Agent, or Firm—Flynn, Thiel, Boutell & Tanis, P.C.

[57] ABSTRACT

A rechargeable battery pack (20) having a plurality of rechargeable cells (30) that form a cell cluster (32). Binders (62) formed of electrically insulating material are secured over the top and bottom of the cells. Each binder is formed with a set of openings (64) that exposed the base (52) of each cell which serves as its negative terminal and its head (54), which serves as its positive terminal. The binders are further shaped so that the perimeter sections that define the openings extend around the cell lips (56) integral with the bases (52) that surround the heads (54). Conductive straps (70) extend between the openings over the binders to electrically connect the cells together. Thus, the binders, in addition to securing the cells together, insulate the straps from the underlying cell lips. This insulating function prevents the straps from shorting out the cells to which they are connected. Insulating tape (60) secured around the side walls (56) of the cells prevent the cells from shorting out upon contact.

32 Claims, 6 Drawing Sheets

1

RECHARGEABLE BATTERY PACK AND METHOD FOR MANUFACTURING SAME

FIELD OF THE INVENTION

This invention relates generally to rechargeable batteries and, more particularly, to a rechargeable battery pack that is durable and economical to provide.

BACKGROUND OF THE INVENTION

Rechargeable battery packs are used to provide the power for many different types of portable, electrically powered tools. The integration of the battery pack into this type of tool eliminates the need to provide the tool with a power cord that is connected to an external power source. One type of tool a rechargeable battery pack is used to power is the cordless surgical tool. The elimination of a cord for a surgical tool offers several benefits over corded surgical tools. Surgical personnel using this type of tool do not have to concern themselves with either sterilizing a cord so that it can brought into the sterile surgical field surrounding the patient or ensuring that, during surgery, an unsterilized cord is not inadvertently introduced into the surgical field. Moreover, the elimination of the cord results in the like elimination of the physical clutter and field-of-view blockage the cord brings to a surgical procedure.

A typical rechargeable battery pack includes a number of rechargeable, current storing cells. The cells of many battery packs are NiCd cells. These cells are connected together to form what is referred to as a cell cluster. The cell cluster is contained within a housing that forms the body of the battery pack. The housing has exposed contacts. The contacts serve as the conductive members through which current is stored in the cell cluster and drawn out of the cell cluster.

A typical rechargeable cell has a cylindrical outer case formed of conductive metal. This case forms the base of the cell as well as the side wall. The case also serves as the negative terminal, the ground terminal, for the cell. A disk-like piece of metal serves as both the head of the cell and the positive terminal. In order to hold the head in place, the metal forming the outer case is bent over to form an annular, inwardly directed lip that extends around the positive terminal. An insulating ring separates the case from the head to prevent these components from shorting out.

During assembly of a cell cluster, the cases of the cells are typically electrically connected to the positive terminals of the adjacent cells. In order to facilitate making these connections and to minimize the size of the battery pack, the individual cells are tightly packed together. Also, some cells are inverted relative to adjacent cells so that the positive terminal, the head, of one cell is adjacent the base of the case of the cell to which it is connected. This makes it possible to electrically connect the cells together in series by securing a strap of conductive material from the base of one cell to the positive terminal of the neighboring cell.

In order to make the above described cell cluster, additional assembly steps are required. First, it is necessary to provide an insulating sleeve around the sides of the individual cells. This insulation prevents short circuits from being established between the cells due to their abutment against each other. It is also necessary to provide a ring of insulation around the outer lip of each cell case that holds the complementary cell positive terminal in place. This insulating ring prevents the conductive strap that extends from the head of a cell from establishing a short circuit with the adjacent lip.

In battery packs not intended for sterilization, paper or cardboard is frequently formed into the insulating sleeves. Each sleeve is dimensioned to extend a slight distance above the top of the case over which it is placed. Then, the portion of the sleeve that extends above the case is bent inwardly to form the insulating ring around the upper lip of the case. In battery packs designed for sterilization, tubular sections of heat shrink plastic are fitted over the cells to serve as insulating sleeves. These sleeves are shrunk over the cells over which they are fitted so that the upper portions of each sleeve extends inwardly and serves as the outer insulating ring. Once the insulating sleeves are fitted over the cells, the conductive straps of metal are welded or otherwise electrically secured between the positive terminals of the cells and the negative terminals of the adjacent cells. These conductive straps, in addition to electrically connecting the cells, hold the cells together to form the cell cluster.

Often, the cells forming a cluster are secured together by a second means in addition to the conductive straps. One reason it is desirable to further secure the cells together is that it makes the cell cluster easy to handle during the subsequent steps of assembling the battery pack. Moreover, the second means for securing the cells together typically restricts the movement of the cells relative to each other to a greater extent than this movement is restricted by the conductive straps. Consequently, this second securement means minimizes the stress imposed on the conductive straps that would otherwise be present if the movement of the cells was left unrestricted. The minimization of this stress results in a like reduction in the likelihood that a conductive strap will separate from one of the cells to which the strap is attached. Such separation would, of course, render an assembled battery pack useless.

To date, different methods have been employed to provide a supplemental securement means for holding a cell cluster together. Some cell clusters are provided with paper or cardboard binders that are adhesively secured to the top and bottom of the cells forming the cluster. Unfortunately, there are some risks associated with employing these binders in battery packs intended to be sterilized through autoclaving. This is because should any moisture penetrate the battery pack housing, it could cause the paper forming the binder to break down. Over time, the binder would decay and simply no longer perform the function for which it was designed. Moreover, the moisture which permeates a paper binder could cause an electrical short to develop.

There have been some attempts to provide cell clusters designed for autoclaving with binders formed of silicone. These binders are formed by applying a semisolid paste to the bottom and top surfaces of a partially assembled cell cluster. Once the paste cures, it forms an adhesive binder that secures the individual cells forming the cluster together. This adhesive binder is capable of withstanding the rigors of autoclaving. However, while this paste-formed binder is useful, it is difficult to manufacture. As discussed above, it is formed out of a semi-solid material. Accordingly, at a facility at which these battery packs are manufactured, the extra process steps that are performed when working with semi-solid materials must be employed. These processes include the cleaning steps that need to be performed on the equipment used to store and discharge the semi-solid paste. The requirement of having to perform these additional steps when manufacturing a rechargeable battery pack invariably adds to the complexity and cost of the manufacturing process.

SUMMARY OF THE INVENTION

This invention relates to an improved battery pack and an improved method for manufacturing a battery pack. More particularly the battery pack of this invention is provided with a binder that can withstand the rigors of autoclaving and that also eliminates the need to fit each cell with a relatively long insulating sleeve. This invention is also directed to a relatively low cost means of assembling a battery pack that eliminates the need to introduce any liquid or semi-solid material into the assembly process.

BRIEF DESCRIPTION OF THE DRAWINGS

The invention is pointed out with particularity in the claims. The above and further features of this invention may be better understood by reference to the following description taken in conjunction with the following drawings in which;

DETAILED DESCRIPTION

Figure 1:
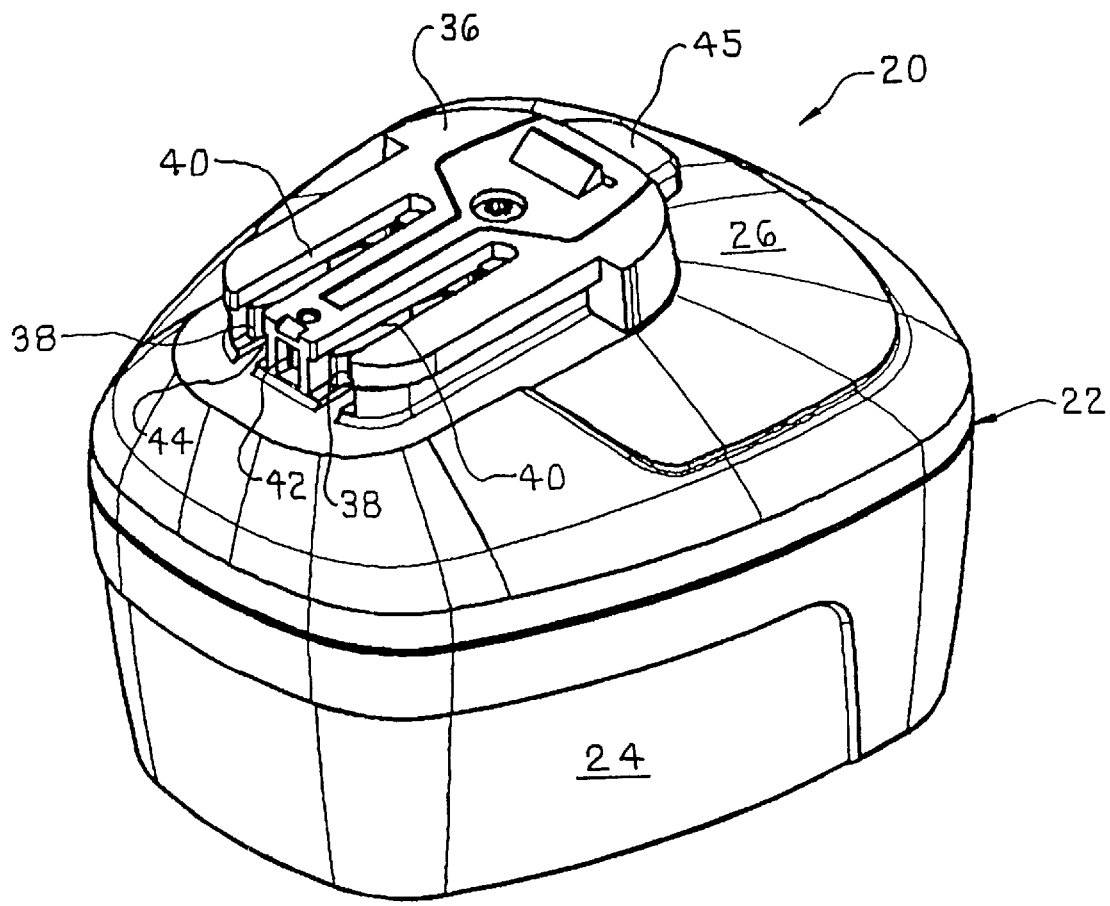
FIG. 1 is a perspective view of a rechargeable battery of this/invention.
Figure 2:
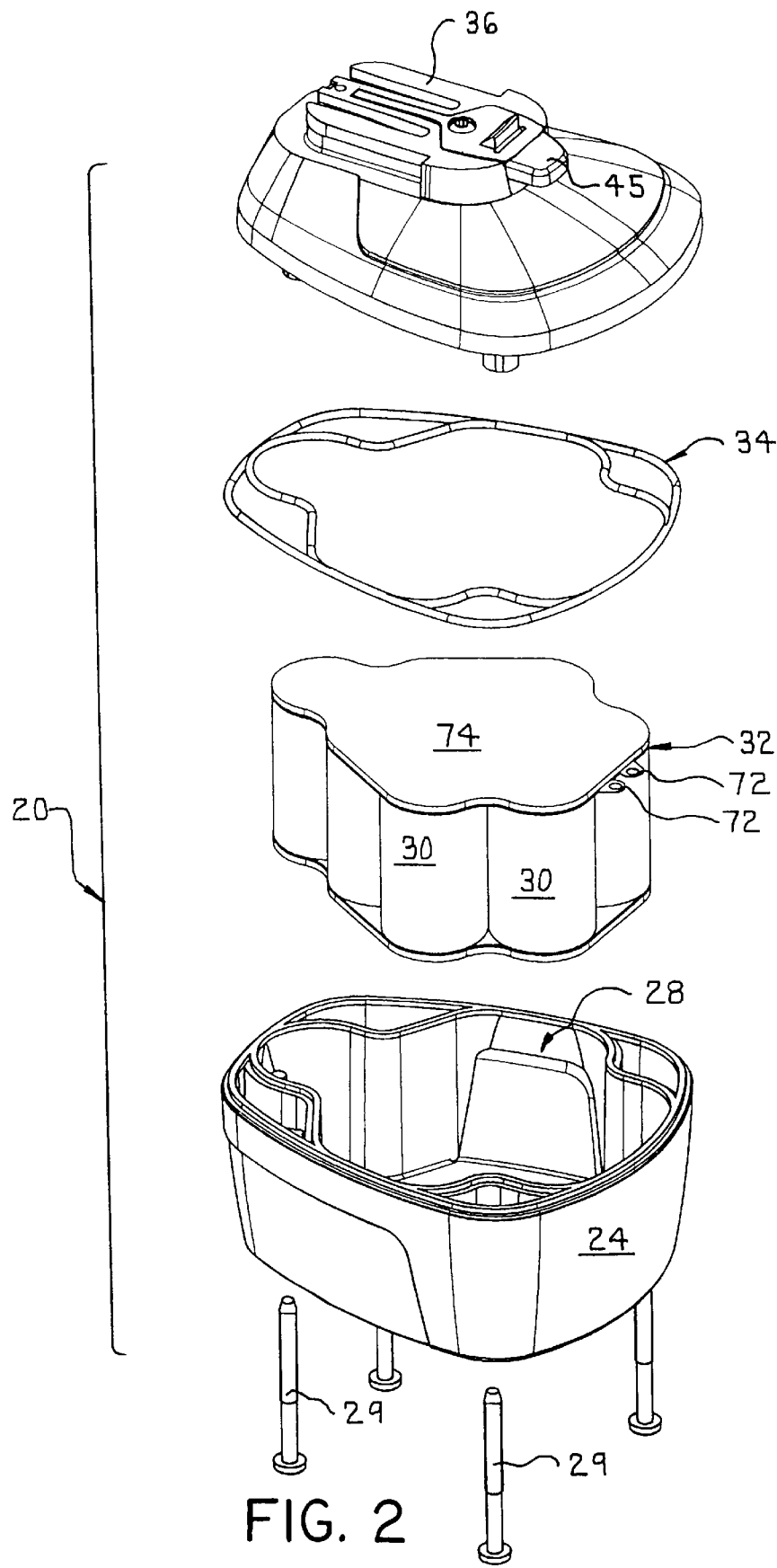
FIG. 2 is an exploded view depicting how a cell cluster is fitted in a battery housing.

FIGS. 1 and 2 illustrate the basic components of a rechargeable battery pack 20 constructed according to this invention. The battery pack 20 includes an outer body 22 formed from a bottom housing 24 and a top housing 26. The bottom housing 24 is formed to define a cavity 28 in which a number of rechargeable cells 30 are seated. The cells 30 are assembled together as a single unit referred to as a cell cluster 32. The cell cluster 32 is enclosed in the bottom housing 24 by top housing 26. A molded O-ring 34 forms a seal between the bottom and top housings 24 and 26, respectively, in order to prevent water vapor from entering into cavity 28. The housing 24 and 26 are held together by fastening screws 29. The material from which the body 22, as well as the other components of the battery pack 20 of this invention, are formed are capable of withstanding exposure to autoclave sterilization wherein the battery is exposed to near 100% humidity at 270° F. at 30 psi.

Top housing 26 is formed to have a head 36. A pair of contact springs 38 are seated in separate slots 40 formed in the head 36. The contact springs 38 function as the conductive elements through which the cells 30 are charged and a current is drawn from the cells. The depicted battery pack 20 has a third contact, a data contact 42, seated in a separate opening 44 in the head 36. Secured inside the top housing 26 is a memory chip with integrated temperature sensor, (not illustrated). Data contact 42 serves as the conductive element through which data is written to this memory chip and from which data is read from the chip. A locking tab 45 is pivotally secured to the top of the head 36. The locking tab 45 secures the battery pack 20 to the complementary power-consuming tool with which it is used.

Figures 3, 3A:
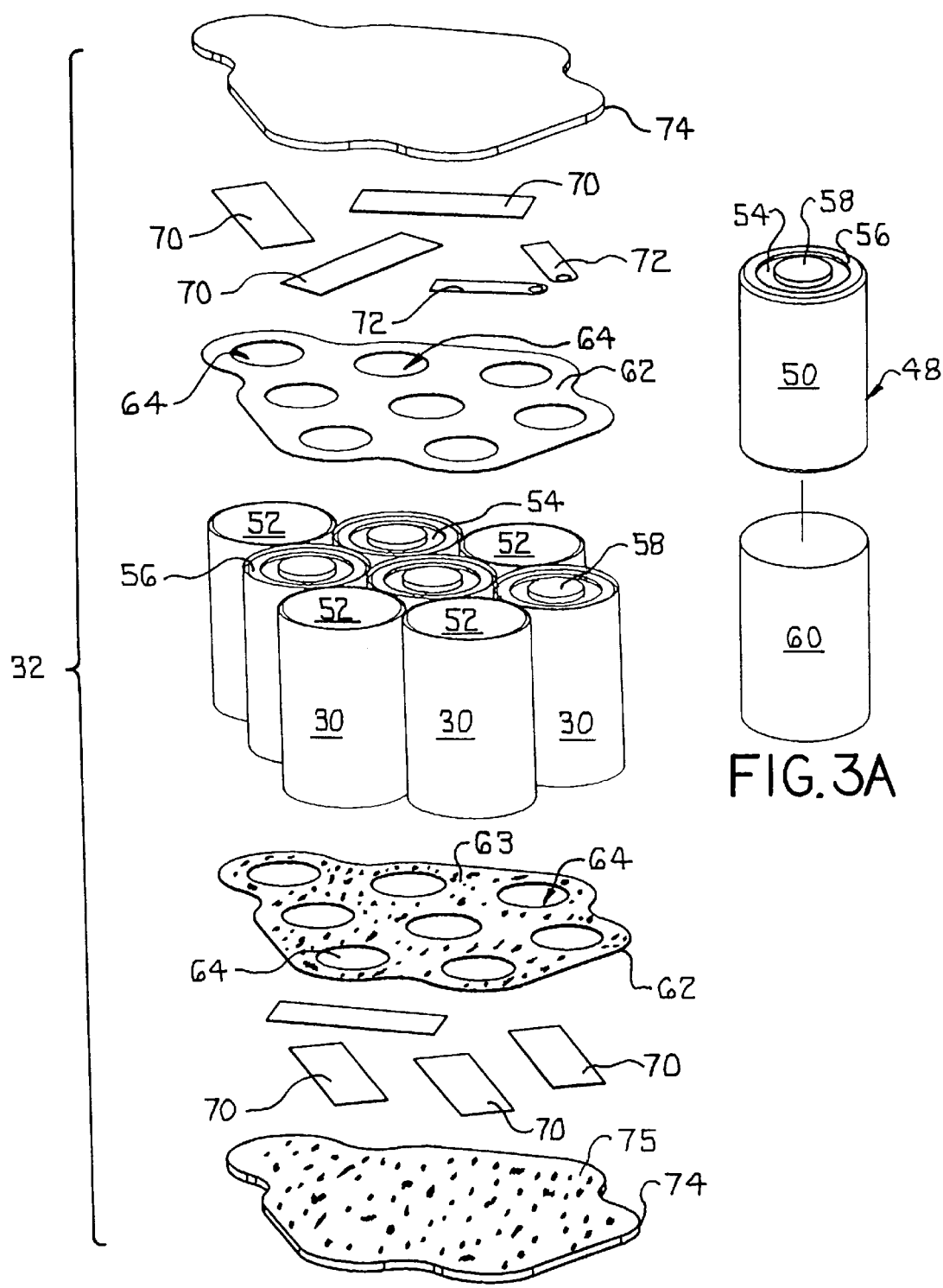
FIG. 3 is an exploded view illustrating the components of the cell cluster.
FIG. 3A is an exploded view illustrating how a insulating tape is fitted around a cell.

Each cell 30, as seen in FIGS. 3 and 3A, is a NiCd cell or other cellular unit capable of storing current. One suitable cell is the N1000SCR manufactured by Sanyo. Each cell 30 has a cylindrical outer case 48. Case 48 forms both the circumferentially extending side wall 50 and base 52 of the cell 30. The case 48 is formed of metal and serves as the negative or ground terminal for the cell 30. The base 52 forms one end of the cell. A generally disk-shaped head 54 forms the top end of each cell 30, the end opposite the base 50. The head 54 is formed of metal and functions as the positive terminal of the cell. In order to hold the head 54 in position, it will be observed that the top of the case 48 is folded inwardly to form a lip 56 that extends around the outer perimeter of the head 54. An insulating ring, (not illustrated) electrically separates the case 48 from the head 54. A boss 58 extends upwardly from the head 54. Boss 58 functions as a raised surface to which a complementary conductive component can be attached.

The depicted cell cluster 32, is formed out of eight closely packed cells 30. It will be observed that, while the cells 30 abut side-to-side, the do not all have the same top-to-bottom orientation. This selective inversion of the cells 30 facilitates their subsequent electrical connection together in series. Insulating tape 60 extends around the side wall 50 of each cell to provide an electrical barrier between the adjacent cell cases 48. In most preferred versions of the invention, the insulating tape is less than 10 mils (0.010 inches) thick. One preferred insulating tape is a polyamide tape, 2 mils thick sold under the trademark KAPTON by DuPont. A silicone adhesive secures tape 60 to the underlying cell side wall. One suitable adhesive is manufactured by A. J. Reynolds as Part. No. 514.

The cells 30 are held together to form the cluster 32 by two binders 62. One binder 62 is located above the cells 30; the second binder 62 is located below the cells. The binders 62 are formed of electrically non-conductive material able to withstand exposure to the autoclaving process. Some plastics less than 50 mils thick serve suitable binders 62. One specific material from which it is possible to form a binder 62 is a plastic formed from polyester sold under the trademark MYLAR by DuPont. It has been found possible to construct suitable binders 62 formed from MYLAR that are 14 mils thick. An adhesive, represented by stippling 63 on the lower of the two binders 62, applied to the binders as part of their manufacturing process, secures the binders to the cells 30. One suitable adhesive is a pressuresensitive acrylic adhesive such as the VHB brand adhesive sold by the 3M Corporation. A removable backing, not illustrated, covers adhesive 63 prior to the manufacture of the cell cluster 32.

Figure 4:
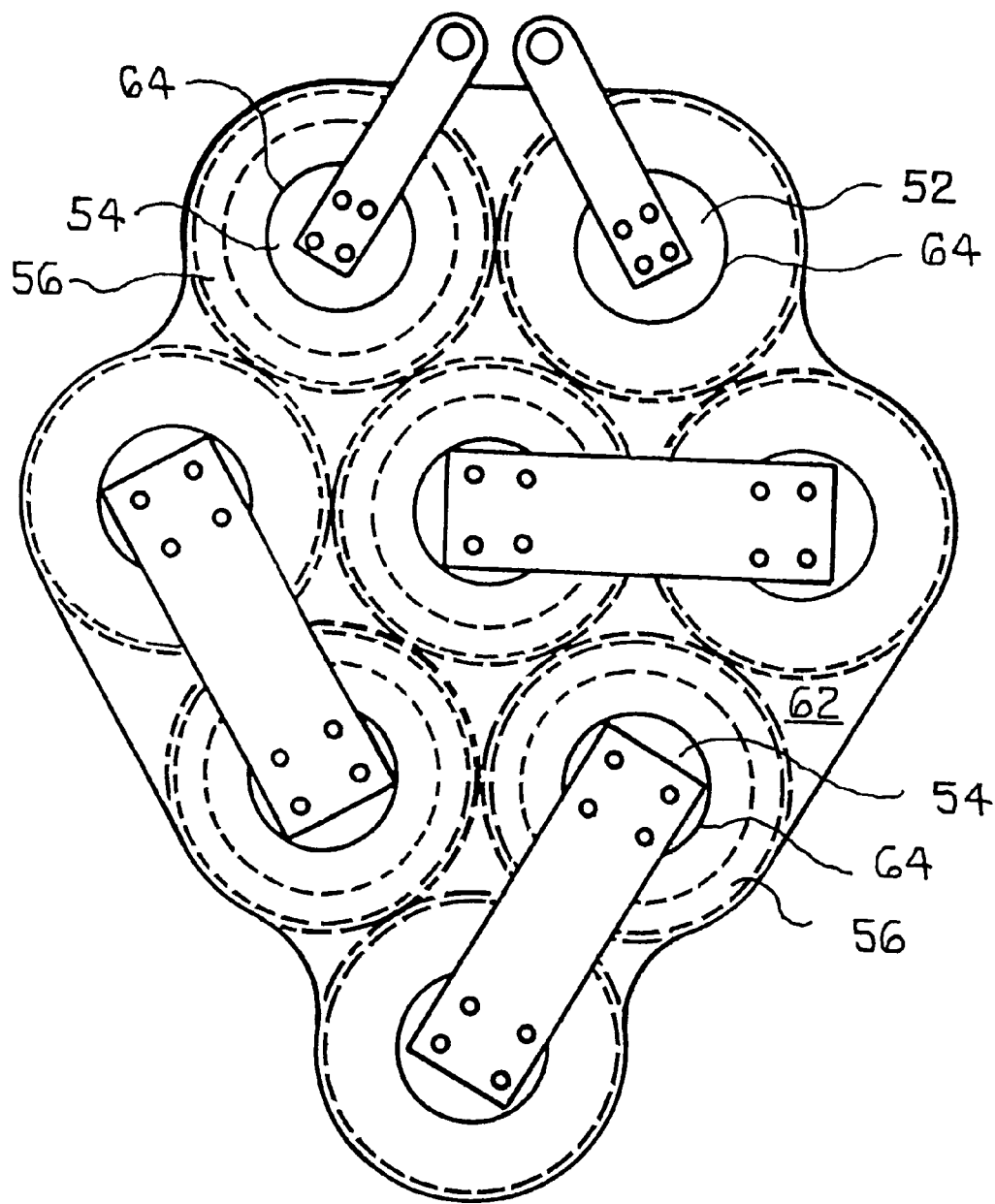
FIG. 4 is a top view of a cell cluster illustrating the relationship between the shape of the binder and the cells the binder is employed to hold together.

It will be observed from FIGS. 3 and 4 that each binder 62 is formed with a number of openings 64. The openings 64 partially expose the bases 52 and heads 54 of the cells 30 subtended by the binders 62. More particularly, each binder 62 is formed so that the circumferential perimeter sections that define the openings 64 over each cell head 54 cover the case lip 56 that extends around the head.

The cells 30 are electrically connected together by conductive straps 70. In one version of the invention, the straps 70 are formed of nickel, or other metal and are approximately 7 mils thick. Each strap 70 extends from the base 52 of one cell to the boss 58 of a second cell. Straps 70 also extend over the adjacent binders 62. Thus, each strap 70 extends from one opening 64 to a second opening 64. The straps 70 are welded, soldered or otherwise electrically connected to the cell bases and bosses 52 and 58, respectively.

It can also be seen in FIG. 3 that the cell cluster 32 is provided with two conductive terminals 72. Each terminal 72 is connected to one cell base 50 or cell boss 58. Terminals 72 function as the conductive elements to which wires are connected in order to establish a conductive path between the contact springs 38 and the cell cluster 32. The terminals 72 are typically formed from the same material from which the straps 70 are formed and have approximately the same thickness as the straps.

Shock absorbers 74 are attached to the top and bottom of the cell cluster 32. Each shock absorber 74 is formed from a sheet of compressible material. One suitable material from which the shock absorbers can be formed is silicone sponge rubber. In some versions of this invention, each shock absorber 74 has a maximum thickness of approximately 100 mils. In more preferred versions of the invention, each shock absorber 74 has a thickness of approximately 60 mils. A pressure-sensitive adhesive, represented by stippling 75 in FIG. 3, binds each shock absorber 74 to the underlying exposed outer surfaces of the adjacent binder 62, the straps 70 and conductive terminals 72. One suitable adhesive 75 is the A25 High Performance brand adhesive manufactured by the 3M Corporation. The adhesive 75 further binds each shock absorber 74 to the portions of the cells 30 exposed through the underlying openings 64.

An initial step in the manufacture of a cell cluster 32 according to this invention is the application of the wrapping of the insulating tape 60 around the cell side walls 50. Since the binders 62 provide the electrical insulation around the top ends of the cells, there is no reason to dimension the insulating tape 60 so that it extends over the cell bases 52 or above the upper ends of the cells side walls 50.

Figure 5:
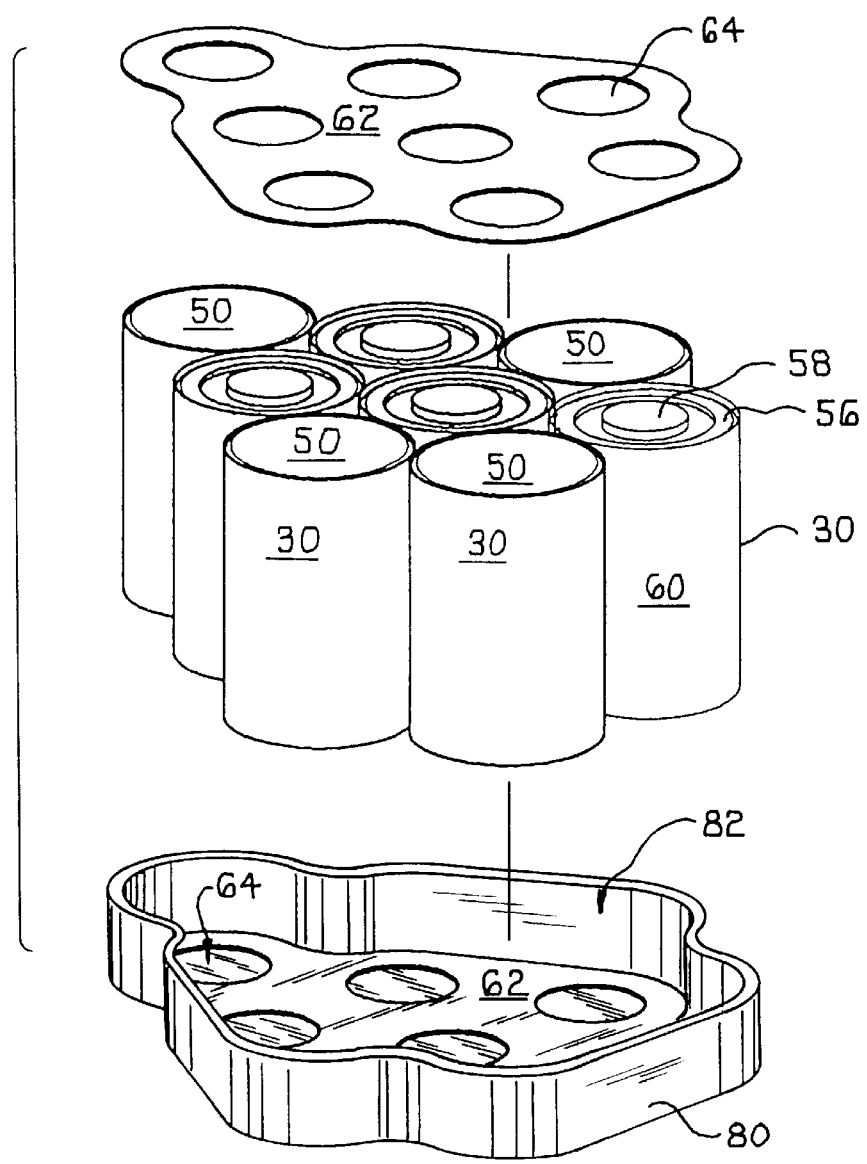
FIG. 5 is an depicts how individual cells are held in a positioning fixture during the manufacture of the cell cluster.

The next step in the manufacture of the cell cluster 32 is the packing of the cells 30 together. This step is performed by placing the cells in a positioning fixture 80 depicted by FIG. 5. The positioning fixture 80 defines a cavity 82 which has the dimensions of the cells when they are closely packed together. In some versions of this method of manufacture, a binder 62, with its adhesive layer 63 exposed, is placed in the base of the cavity 82 prior to the placement of the cells. In these versions of the invention, the placement of the clustering of the cells together in the positioning fixture 80 results in the simultaneous securement of the cells to one of the binders 62. Once the cells are clustered in the positioning fixture 80, a binder 62 is secured to the exposed cell bases and case lips 52 and 56, respectively, to secure the cells together. Once the cells 30 are packed together, the cells are collectively referred to as a cell array.

After the basic cell array is formed, the straps and conductive terminals 70 and 72, respectively, are secured in place. The straps 70 and conductive terminals 72 are secured in place by welding, soldering or any other means that ensures conductive contact is made between these components and the associated conductive components of the cells 30.

Next, a shock absorber 74 is secured to the partially assembled cluster on the side opposite the conductive terminals 72. This step is performed by pressing the adhesive-coated surface of the shock absorber 74 against the complementary surfaces of the cells 30, the binder 62 and the straps 70.

Next, the wires are attached to the conductive terminals 72. The wires may then be connected to the contact springs 38. Once the wires are attached to the conductive terminals 72, the second shock absorber 74 is secured to the side of the assembly from which the terminals 72 extend. This completes the assembly of the cell cluster 32.

The cell cluster 32 is then placed in the bottom housing 24. The housings 24 and 26 are then secured together to complete assembly of the battery pack 20.

The binders 62 integral with the cell cluster 32 of battery pack 20 of this invention perform several functions. First, the binders 62 hold the cells 30 forming the cluster together. Given the strength with which the binders 62 hold the cells together, a cell cluster constructed according to this invention is relatively easy to handle during the subsequent steps of the battery pack assembly process. Moreover, since binders 62 hold the cells together, the means employed to secure the straps 72 to the cells does not have to do double duty as a means for holding the cells together. Consequently, relatively inexpensive means such as spot welding may be employed to electrically connect the cells 30. Also, since the binders 62 hold the cells 30 together, the likelihood that post manufacture, in-use cell vibration will cause strap separation is substantially eliminated.

The binders 62 also serve as the insulating members that surround the lips 56 of the cell cases 48 that surround the heads 54. Thus, the insulating tape 60 does not have to be applied to the cells so that it extends over the case lips 56. This eliminates both the need to provide relatively wide sections of insulating tape as well as the process step required to apply the tape so that it extends over the case lips 56.

Still another feature of this invention is that the insulating tape 60, the binders 62 and shock absorbers 74 each arrive at the assembly process with their adhesive layers pre-applied. Thus, the cell cluster/battery pack assembly process of this invention does not employ liquid or semi-solid materials. Therefore, the application, cleaning and control steps associated with the use of these materials form no part of this assembly process.

Thus, a battery pack assembled according to this invention is both relatively durable and economical to manufacture.

Figure 6:
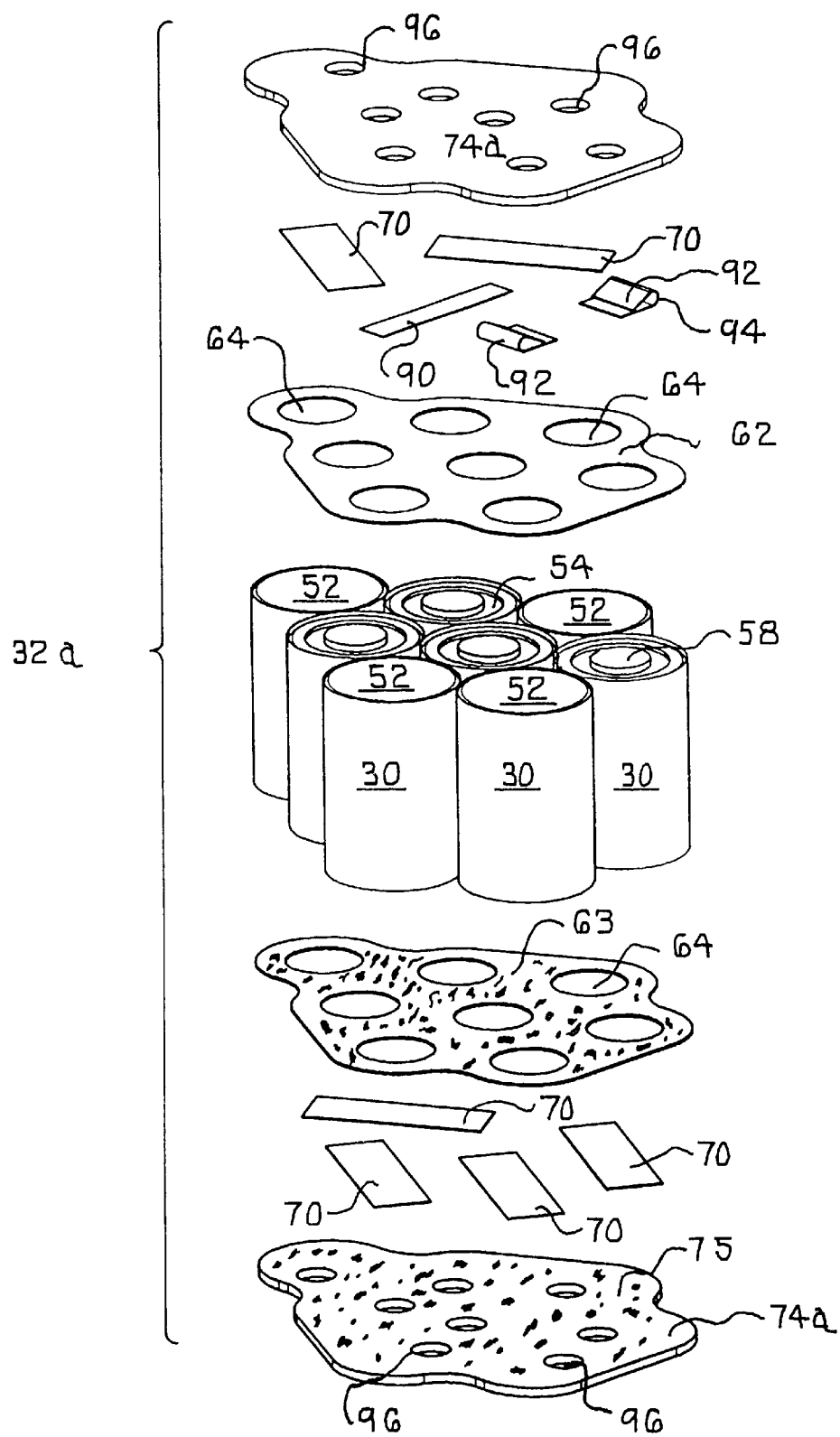
FIG. 6 is an exploded view of an alternative cell cluster of this invention.

FIG. 6 illustrates an alternative cell cluster 32a constructed in accordance with this invention. Cell cluster 32a includes the same basic cells 30, insulating tape 60 and binders 62 of the first described embodiment of this invention. Also, conductive straps 70 secure most, but not all, of the cells 30 together.

Cell cluster 32a, also includes one or more fuse straps 90, one shown, for securing some of the cells together. Each fuse strap 90 is formed out of material that will separate when current flow therethrough exceeds a selected amperage. In one version of the invention, the fuse strap 90 is formed from the same material from which the conductive straps 70 are formed. However, the fuse strap is formed out of a thinner strip of metal that has a narrower width than the metal forming the associated conductive straps 70. For example, when the conductive straps 70 and fuse strap 90 are formed from nickel, the fuse strap has a thickness of 5 mils and a width of 200 mils. This particular fuse strap will separate when current flow through it exceeds approximately 140 Amps.

An advantage of providing the cell cluster 32a with fuse straps 90 is that they prevent excessive current flow through the battery.

Cell cluster 32a is also provided with terminals 92 to which the wires are connected for establishing a connection to the contact springs 38. Each terminal 92 is formed from a flat strip of metal that is rolled over at one end to define channel 94. An exposed end of the associated wire is seated in the channel 94 and soldered or otherwise permanently secured in place. The exposed end of the wire integral with terminal 92 is soldered in channel 94. Each terminal 92 does not extend beyond the perimeter of the end of the cell 30 to which the terminal is attached. Consequently, the metal forming the terminal 92 is not bent by any vibration or movement of the complementary wire. This arrangement minimizes the structural fatigue to which the terminal 92 is exposed so as to substantially eliminate that likelihood that it could be subjected to structural failure.

Moreover, the shock absorber 74a is secured over the partially assembled cell cluster after the wires are connected to the terminals 92. Consequently, the shock absorber 74a covers the ends of the wires that extend away from the terminals. Thus, shock absorber 74a provides insulation between the terminals 92 and the wires and the memory chip or other components that may be located immediately above the terminals.

Shock absorber 74a of this embodiment of the invention is structural very similar to previously described shock absorber 74. Shock absorber 74a is however formed to define openings 96 that extends through the shock absorber. Holes 96 are positioned to be centered over small vents formed between the heads 54 and lips 56 of the cells 30, (vents not illustrated). Thus, the holes 96, which have a diameter of approximately 0.250 inches, partially overlap and are axially offset from the openings 64 formed in the binders 62. Holes 96 allow any gas released by the cells 30 to be vented through the cell cluster 32a so that the gas can be released out of the battery pack 20.

It should be recognized that the foregoing description is for the purposes of illustration only. It will be readily understood that alternative constructions of the battery pack 20 of this invention can be provided and that there are alternative steps for manufacturing the battery pack. For example, it may be desirable to construct a battery pack in which some or all of the cells are connected together in parallel. With such a battery pack, it may not be necessary to provide insulating tape around some of the cell side walls 50 to establish a ground plane extending across the cells. If the cells 30 are all connected together in parallel, the cells would have a common top-to-bottom orientation and the straps 70 would extend between the cell bosses 58. In these versions of the invention, it may also only be necessary to provide a single binder 62 with openings 64. This binder would be extend over the head ends of the cells.

Also, the types of material from which the components are formed, the stated dimensions and the number of cells should be understood to only be exemplary. For example, if a battery pack 20 is not designed to be subjected to autoclaving, it is usually not necessary to form the components out of material designed to withstands the high heat, high humidity environment of the autoclave. Thus, some battery packs 20 of this inventions be provided with insulating sleeves formed from paper or other material less expensive than the described polyamide tape. Also, the binders 62 of these batteries may be formed out of material such as paper or fiber.

It should similarly be recognized that cells having a construction different from what has been described may be employed in the battery pack of this invention. For example, not all cells have lips that hold the complementary cell heads 56 in place. Nevertheless, the binders 62 still cover the upper ends of the cell side walls 50 that surround the heads 56 to prevent the conductive straps 70 from shorting out the individual cells.

Moreover, the materials and dimensions of the other components may vary. In still other versions of the invention, the heat shrink tubing may be employed as the insulating sleeves. Also, in some versions of the invention, owing to the material from which the insulating sleeves are formed and the means by which the material is secured to the cases 48, the sleeves may partially cover the bases 52 and/or lips 56 of the cases 48. Nevertheless, any base or lip surface of the cases 48 remains exposed will, of course, be insulated by the binder 62 that covers that end of the cell.

It should likewise be recognized that the method of manufacture may vary from what has been described. For example, it may not be desirable to place a binder 62 in the positioning fixture 80 prior to the insertion of the cells 30. In this version of the method of manufacture, once the binder 62 is affixed to the exposed cell bases and case lips 52 and 56, respectively, the partially assembled cell cluster 32 is removed from the positioning fixture 80. The cell cluster 32 is then inverted and the remaining binder 62 secured in place.

Therefore, it is the object of the appended claims to cover all such modifications and variations as come within the true spirit and scope of this invention.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A rechargeable battery pack, said battery pack including:
   a housing;
   a cell cluster disposed in said housing, said cell cluster including:
      a cell array formed from a plurality of rechargeable cells, each said cell having: a conductive case that serves as a first terminal of said cell, wherein said case has a base that forms one end of said cell; and a conductive head opposite said base that serves as a second end of said cell, wherein said case is formed to have a lip that extends around a perimeter of said head and said cells are arranged together in a side-by-side arrangement, wherein said cell array has opposed ends formed from said bases and said heads of said cells;
      a flat binder formed from electrically insulating material that is secured to one end of said cell array to secure said cells together, said binder extending over at least one said cell head, said binder being formed with a plurality of openings, each said opening exposing an end of one of said cells which said binder subtends, wherein said binder includes a section that subtends said case lip located around said cell head subtended by said binder; and
      a conductive strap extending between two said cells subtended by said binder, said conductive strap extending from said cell head, through said binder opening through which said cell head is exposed, over said binder, into a second binder opening and to an end of a second said cell; and
   a plurality of exposed, conductive contacts secured to said housing, said conductive contacts being electrically connected to said cells of said cell cluster.

2. The rechargeable battery pack of claim 1, wherein:
   each said cell case forms a side wall that extends from said base to said lip and each said cell case side wall is encased in an electrically insulating sleeve; and
   said cells are arranged in said cell cluster so that a head of a first said cell is located adjacent a base of a second cell and said side walls of said first and second cells abut each other; and said binder extends over said head of said first cell and said base of said second cell and said conductive strap extends between said head of said first cell and said base of said second cell.

3. The rechargeable battery pack of claim 2, further including a foam layer disposed over said binder, said conductive strap and said cell ends exposed by said binder openings.

4. The rechargeable battery pack of claim 1, wherein:

each said cell case forms a side wall that extends from said base of cell to said lip and each said cell case side wall is encased in an electrically insulating sleeve;

said cell array includes at least three said cells wherein said heads of two said cells are located adjacent said base of an at least one remaining cell to form a first end of said cell array and said bases of said two cells are located adjacent said head of said at least one remaining cell to form a second end of said cell array and each said cells abuts at least one other said cell;

a first said binder extends over the first end of said cell array and a second said binder extends over the second end of said cell array, each said binder being secured to said cell ends over which said binder extends to secure said cells together and being formed with openings that partially expose said cell ends, wherein said binders include portions that subtend said case lips; and a plurality of said conductive straps electrically connect said cells together in series, wherein each said conductive strap extends over one of said binders.

5. The rechargeable battery pack of claim 4, wherein said binders are formed from plastic and are adhesively secured to said cells.

6. The rechargeable battery pack of claim 4, wherein said cell cluster further includes first and second foam layers, each said foam layer being secured to a separate one of said binders.

7. The rechargeable battery pack of claim 4, wherein said insulating sleeves are formed from electrically insulating tape and said tape is positioned over said cells to expose said case bases and said case lips.

8. The rechargeable battery pack of claim 4, wherein two of said cells are series connected together by a fuse that opens when current flow through said fuse exceeds a selected current.

9. The rechargeable battery pack of claim 1, wherein said binder is formed from plastic.

10. The rechargeable battery pack of claim 1, wherein said cell cluster further includes a foam layer that is adhesively secured over said binder so as to be located between said binder and an adjacent portion of said housing.

11. The rechargeable battery pack of claim 1, wherein each said cell case has a side wall and electrically insulating tape is adhesively secured to said cell side walls, wherein said insulating tape is secured to said cells to expose said case lips.

12. A rechargeable battery pack, said rechargeable battery pack having:

a housing;

a cell cluster, said cell cluster including:

a cell array formed from at least three rechargeable cells, each said cell having: a conductive case that defines a cell base and a cell side wall; and a head, separate from said case, that is located opposite said base, wherein said case includes a lip that extends around said head and said case, including said base, forms a first terminal of said cell and said head forms a second terminal of cell and said cells are arranged together side-by-side to form said cell array and are oriented so that the bases of two said cells and the head of an at least one remaining said cell form a first end of said cell array and the heads of said two cells and the base of said at least one remaining cell form a second end of said cell array, and said each said cell abuts at least one other said cell;

a plurality of insulating sleeves, each said insulating sleeve extending around said side wall of a separate said cell so that said insulating sleeves insulate said cell cases from each other, wherein said insulating sleeves are disposed over said cell cases so as to leave said bases and said lips of each said cell at least partially exposed;

two binders, each said binder being formed from flat, electrically insulating material and being disposed over a separate one of said ends of said cell array, each said binder being adhesively bonded to said cell bases and case lips over which said binder is disposed to secure said cells together, each said binder being formed with a plurality of openings, each opening exposing one of said cell bases or said heads wherein, said binders are formed with sections that subtend said case lips;

a plurality of conductive straps for electrically, series connecting said cells together, each said strap extending from a cell base, through one said binder opening, over said binder, through a second binder opening and to a cell head adjacent said cell base; and two conductive terminals, each said terminal extending from a cell head or a cell base through a binder opening; and conductive contacts secured to said housing, said conductive contacts being electrically connected to said conductive terminals of said cell cluster to establish an electrical path from said conductive contacts to said cells.

13. The rechargeable battery pack of claim 12, wherein said insulating sleeves are formed from insulating tape that is adhesively secured to said side walls of said cells.

14. The rechargeable battery pack of claim 12, wherein said binders are formed from plastic.

15. The rechargeable battery pack of claim 12, wherein said cell cluster further includes first and second foam layers, each said foam layer being secured to a separate one of said binders.

16. A rechargeable battery pack, comprising:

a cell cluster, said cell cluster including:

a cell array formed from a plurality of rechargeable cells, each said cell having: a conductive case that is shaped to define a base, a side wall that extends upwardly form said base that has an upper end distal from said side wall, wherein said case is a first conductive terminal of said cell; and a head secured to said case adjacent said upped end of said side wall, wherein said head is electrically insulated from said case and functions as a second conductive terminal of said cell and wherein said cells are positioned together so that said case side wall of at least one cell abuts a case side wall of a second cell;

an insulating sleeve adhesively secured to each said case side wall to electrically insulate said abutting case side walls from each other, each said insulating sleeve formed from an electrically insulating tape that is adhesively secured to said case side wall with which said sleeve is associated;

a binder secured over said cells, said binder being formed from electrically insulating material and adhesively secured over one end of said cells so as to secure said cells together, said binder being formed with openings that expose the heads of said cells subtended by said binder, wherein each said binder opening is defined by a section of said binder that subtends said case upper end; and a conductive strap for electrically connecting a head of a first said cell to an adjacent end of a second said cell, said conductive strap extending from said binder opening through which said head of said first cell is exposed, over said binder and into said binder opening through which said end of said second cell is exposed;

a housing having an enclosure in which said cell cluster is contained; and conductive contacts that are mounted to said housing and electrically connected to said cells.

17. The battery pack of claim 16, wherein: said cells are arranged so that said head of said first cell is located adjacent said base of said second cell; and said conductive strap extends from said head of said first cell, over said binder to said base of said second cell.

18. The battery pack of claim 16, wherein: each said cell case is formed with a lip that extends inwardly from said upped end of said case side wall so that said lip at least partially surrounds an outer perimeter of said head of said cell; and portions of said binder that define said openings through which said heads are exposed cover said lips of said cell cases.

19. The battery pack of claim 16, wherein: said cell cluster further includes a conductive terminal attached to one of said cells, said conductive terminal establishing a conductive path between said cells and one of said conductive contacts; and said binder is formed with an opening that exposes a portion of said cell to which said conductive terminal is attached.

20. The rechargeable battery pack of claim 16, wherein two of said cells are series connected together by a fuse that opens when current flow through said fuse exceeds a selected current.

21. A method of assembly a cell cluster, said method including the steps of:

providing a plurality of rechargeable cells, each cell having: a case that defines a base which functions as one end of the cell, a side wall that extends upwardly from the base, the side wall having an upper end located distal from said base; and a head mounted to the case so as to function as a second end of the cell, wherein the upper end of the side wall extends around an outer perimeter of the cell head and the case and the cell head function as separate electrical terminals of the cell;

arranging the cells in a side-by-side arrangement so that the side wall of each cell abuts the side wall of another cell and the cells form a cell array that has opposed ends formed from the opposed ends of the cells;

securing a planar, electrically insulating binder over at least one end of the cell array that has at least one cell head, wherein the binder secures the cells together and the binder is formed to define openings that at least partially expose the ends of the cells and the portion of the binder that defines the opening that exposes the cell head covers the upper end of the cell side wall associated with the exposed cell head; and electrically connecting the cell head to the end of adjacent cells by securing a conductive strap between the cell head and the adjacent cell end, wherein the strap extends from a first binder opening, over the binder and into a second binder opening.

22. The method of manufacturing a cell cluster of claim 21, wherein said binder is adhesively secured to the cells.

23. The method of manufacturing a cell cluster of claim 21, further including the step of placing an insulating sleeve over the side walls of the cells prior to said arrangement of the cells together so that the cases of adjacent, abutting cells are electrically insulated from each other.

24. The method of manufacturing a cell cluster of claim 23, wherein said step of placing an insulating sleeve over the side walls of the cells comprises the step of adhesively securing an insulating tape around the cell side walls.

25. The method of manufacturing a cell cluster of claim 23, wherein: during said arrangement of the cells, at least two adjacent cells are arranged to have opposed base-to-head orientations so that each end of the cell array is formed from at least one case base and one cell head; and during said electrical connection of the cells, cells are connected together in series by connecting a conductive strap at one end to the cell head of the first one of the cells, extending the conductive strap over the binder and connecting the conductive strap at a second end to the base of the adjacent second cell.

26. The method of manufacturing a cell cluster of claim 21, wherein, after step of securing the conductive straps, a cushion layer is secured over the binder and the conductive straps.

27. The method of manufacturing a cell cluster of claim 21, wherein, two binders are secured to the cell array, each binder being secured to a separate end of the cell array, and each binder holds the cells together and is formed with openings that at least partially expose the cell ends that form the end of the cell array covered by the binder.

28. The method of manufacturing a cell cluster of claim 27, wherein: during said arrangement of the cells, at least two adjacent cells are arranged to have opposed base-to-head orientations so that each end of the cell array is formed from at least one case base and one cell head; and during said electrical connection of the cells, two cells are connected together in series by connecting a conductive strap at one end to the cell head of the first one of the cells, extending the conductive strap over the binder and connecting a second end of the conductive strap to the base of the adjacent second cell.

29. The method of manufacturing a cell cluster of claim 21, wherein during said cell arrangement step, the cells are placed in a positioning fixture having an opening that defines a shape of the cell array.

30. The method of manufacturing a cell cluster of claim 29, wherein said binder securement step is performed while the cells forming the cell array remain in the position fixture by placing the binder over an end of the cell array that extends outwardly from the positioning fixture.

31. The method of manufacturing a cell cluster of claim 29, wherein said binder securement step is performed by placing a first binder with an adhesive coating in a base of the positioning fixture prior to said cell arrangement step so that, as each cell is placed in the positioning fixture, the cell is secured to the binder.

32. The method of manufacturing a cell cluster of claim 29, wherein said binder securement step, after said arrangement of the cells, includes securing a second binder with an adhesive coating over an end of the cell array that extends out the positioning fixture prior to the removal of the cell array from the positioning fixture.

* * * * *